(12) United States Patent
Hsieh et al.

(10) Patent No.: US 9,073,833 B1
(45) Date of Patent: Jul. 7, 2015

(54) OXIME-BASED COMPOUND, PHARMACEUTICAL COMPOSITION CONTAINING THE SAME AND METHOD FOR PREPARING THE SAME

(71) Applicant: Chang Gung University, Tao-Yuan (TW)

(72) Inventors: Pei-Wen Hsieh, Tao-Yuan (TW); Tsong-Long Hwang, Tao-Yuan (TW); Wen-Hui Wang, Taichung (TW); Ting-Yi Wang, Taipei (TW)

(73) Assignee: Chang Gung University, Tao-Yuan (TW)

( * ) Notice: Subject to any disclaimer, the term of this patent is extended or adjusted under 35 U.S.C. 154(b) by 0 days.

(21) Appl. No.: 14/528,511

(22) Filed: Oct. 30, 2014

(30) Foreign Application Priority Data

Jan. 24, 2014 (TW) .............................. 103102695 A

(51) Int. Cl.
| | | |
|---|---|---|
| *A61K 31/22* | (2006.01) | |
| *C07C 69/353* | (2006.01) | |
| *C07C 311/29* | (2006.01) | |
| *C07C 303/36* | (2006.01) | |

(52) U.S. Cl.
CPC ............. *C07C 311/29* (2013.01); *C07C 303/36* (2013.01)

(58) Field of Classification Search
CPC .............................. C07C 311/29; C07C 303/36
See application file for complete search history.

(56) References Cited

U.S. PATENT DOCUMENTS 5,017,610 A * 5/1991 Imaki et al. .................... 514/546

FOREIGN PATENT DOCUMENTS

EP 0347168 B1 9/1993

OTHER PUBLICATIONS

Andrew S. Cowburn et al. "Advances in Neutrophil Biology." Chest (2008) 134: 606-612.
Brice Korkmaz et al. "Neutrophil Elastase, Proteinase 3 and Cathepsin G: Physicochemical Properties, Activity and Physiopathological Functions." Biochimie 90 (2008) 227-242. (Available online Oct. 25, 2007).
Brice Korkmaz et al. "Relevance of the Mouse Model as a Therapeutic Approach for Neutrophil Proteinase 3—Associated Human Diseases." International Immunopharmacology (2013) < http://dx.doi.org/10.1016/j.intimp.2013.07.003>.
Brice Korkmaz et al. "Neutrophil Proteinase 3 and Dipeptidyl Peptidase I (Cathepsin C) as Pharmacological Targets in Granulomatosis with Polyangiitis (Wegener granulomatosis)." Semin Immunopathol (2013) 35:411-421.
Kyoung Ja Kwon et al. "Proteinase 3 Induces Oxidative Stress-Mediated Neuronal Death in Rat Primary Cortical Neuron." Neuroscience Letters 548 (2013) 67-72.
Mineji Hayakawa et al. "Sivelestat (Selective Neutrophil Elastase Inhibitor) Improves the Mortality Rate of Sepsis Associated with Both Acute Respiratory Distress Syndrome and Disseminated Intravascular Coagulation Patients." Shock (2010) vol. 33, No. 1, pp. 14-18.
Yoritaka Nakano et al. "Prevention of Leukocyte Activation by the Neutrophil Elastase Inhibitor, Slvelestat, in the Hepatic Microcirculation After Ischemia-Reperfusion." Journal of Surgical Research (2009)155, 311-317. (Submitted for publication Mar. 18, 2008).
Han Hsiang, Wang. "The Structure-Activity Relationships Study of Anti-Inflammatory Activity Anthranilate Derivatives." Graduate Institute of Natural Products of Chang Gung University. Master Thesis. Jul. 2010. (Including English abstract).

* cited by examiner

*Primary Examiner* — Paul A Zucker
(74) *Attorney, Agent, or Firm* — Cesari and McKenna, LLP

(57) ABSTRACT

An oxime-based compound having the following formula (I) or a pharmaceutically acceptable salt thereof:

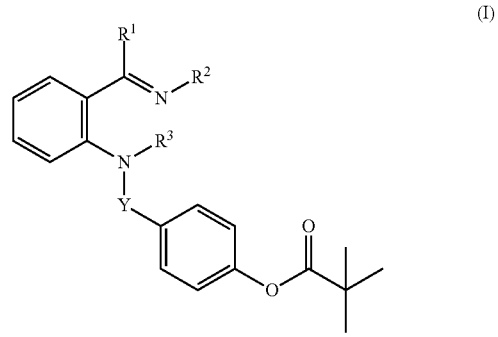

(I)

wherein:
Y is a carbonyl group or a sulfonyl group;
$R^1$ is selected from H, OH, a $C_1$-$C_4$ alkyl group, and a $C_1$-$C_4$ alkoxyl group;
$R^2$ is selected from OH, a methoxyl group, —$OR^4OH$, and —$OR^4NH2$, $R^4$ being a $C_1$-$C_3$ alkyl group; and
$R^3$ is H or a pivaloyloxybenzenesulfonyl group.

16 Claims, 3 Drawing Sheets

OXIME-BASED COMPOUND, PHARMACEUTICAL COMPOSITION CONTAINING THE SAME AND METHOD FOR PREPARING THE SAME

CROSS-REFERENCE TO RELATED APPLICATIONS

This application claims priority of Taiwanese Patent Application No. 103102695, filed on Jan. 24, 2014.

BACKGROUND OF THE INVENTION

1. Field of the Invention

This invention relates to an oxime-based compound, more particularly to a 2-aminobenzaldehyde oxime compound that exhibits anti-inflammatory effect, a method for preparing the same, and a pharmaceutical composition containing the same.

2. Background Information

Neutrophils play a vital role in the defense of a human body against infections. In is response to inflammatory stimulus, activated neutrophils secrete a series of cytotoxins, such as superoxide anion ($O_2.^-$), precursors of other reactive oxygen species, serine proteases, and bioactive lipids.

The molecular weights of neutrophil elastase (NE, also known as leukocyte elastase or lysosomal elastase) (EC 3.4.21.37) and proteinase 3 (also known as leukocyte proteinase 3) (EC 3.4.21.76) are 29-33 kDa and 29-32 kDa, respectively. Both neutrophil elastase and proteinase 3 belong to chymotrypsin-like serine proteinase and are usually stored in azurophil granules of the neutrophils.

The activities of neutrophil elastase and proteinase 3 are modulated by endogenous inhibitor protein (such as α1-protease inhibitor and α2-macrogloblin) in the body to maintain homeostasis. The excessive proteases release may cause tissue damage, and prolonged neutrophil accumulation has an important role in the pathogenesis of inflammatory disorders.

The inflammatory disorders related to neutrophil elastase and proteinase 3 include lung injury (such as acute lung injury), chronic obstructive pulmonary disease, acute respiratory distress syndrome, emphysema, cystic fibrosis, focal cerebral ischemic, ischemic-reperfusion injury, glomerulonephritis, arthritis (such as rheumatoid arthritis), bullous pemphigoid, sepsis and Wegener's granulomatosis (see B. Korkmaz et al. (2008), *Biochimie*, 90:227-242; A. S. Cowburn et al. (2008), *Chest*, 134:606-612; Y. Nakano et al. (2009), *Journal of Surgical Research*, 155:311-317; M. Hayakawa et al. (2010), *Shock*, 33:14-18; K. J. Kwon et al. (2013), *Neurosci. Lett.*, 548:67-72; B. Korkmaz et al. (2013), *Semin. Immunopathol.*, 35:411-421; B. Korkmaz et al. (2013), *Int. Immunopharmacol.*, doi: 10.1016/j.intimp.2013.07.003). Therefore, inhibition of neutrophil elastase and proteinase 3 plays an important role in the design of a drug for inflammatory disorder treatment.

Sivelestat (marketed as Elaspol) is an inhibitor for neutrophil elastase. However, the manufacturing process for sivelestat is complex and hazardous, and sivelestat has a lesser pharmacokinetic effect and is a potential toxin for organs, thereby limiting its use in clinical applications. Sivelestat is currently used for treatment of acute respiratory distress syndrome-related respiratory failure in Japan and Korea (T. Stevens et al. (2011), *The Journal of Pharmacology and Experimental Therapeutics*, 339:313-320).

EP 0347168 B1 discloses phenyl ester derivatives of pivalic acid having a general formula (I) as follows:

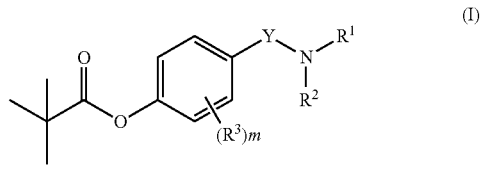

Each group of the phenyl ester derivatives of formula (I) is defined as that in the disclosure of EP 0347168 B1. From Table 1 of EP 0347168 B1, twenty compounds are proven to exhibit inhibitory effect on the activity of neutrophil elastase. The following two compounds are included in the twenty compounds:

Example 2(63): N-[O-(p-pivaloyloxybenzene)sulfonylaminobenzoyl]glycine, wherein $R^1$ is

$R^2$ is H, $R^3$ is H, m is 1, and Y is $SO_2$; and

Example 5(3): p-[N-(O-carboxyphenyl)sulfamoyl]phenyl ester of pivalic acid, wherein $R^1$ is

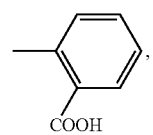

$R^2$ is H, $R^3$ is H, m is 1, and Y is $SO_2$.

Han-Hsiang Wang disclosed several anthranilate derivatives, in which compounds WHH51, WHH52, and WHH53 having the following general formula (II) were proven to be capable of effectively inhibiting release of neutrophil elastase (see the thesis of "The Structure-activity Relationships Study of Anti-inflammatory Activity Anthranilate Derivatives," Graduate Institute of Natural Products, Chang Gung University (2010)).

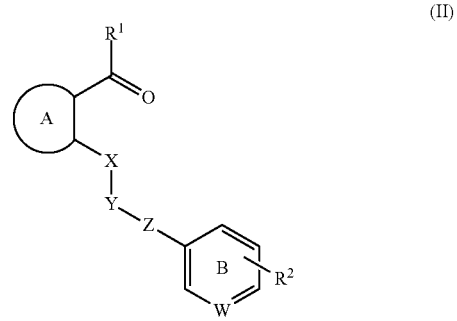

In compound WHH51, ring A is benzene ring, $R^1$ is $OCH_3$, $R^2$ is 4-$OCOC(CH_3)_3$, W is CH, X is NH, Y is $SO_2$, and Z is a single bond. In compound WHH52, ring A is benzene ring, $R^1$ is $OCH_2CH_3$, $R^2$ is 4-$OCOC(CH_3)_3$, W is CH, X is NH, Y is $SO_2$, and Z is a single bond. In compound WHH53, ring A is benzene ring, $R^1$ is $NHCH_2COOCH_3$, $R^2$ is 4-$OCOC(CH_3)_3$, W is CH, X is NH, Y is $SO_2$, and Z is a single bond.

The manufacture of the abovementioned derivatives having formulas (I) and (II) is complex and hazardous due to the use of hydrogen gas. Moreover, the effects thereof on inhibition of proteinase 3 and on treatment of inflammation disorders in vivo have not been proven. Therefore, there is a need in the art to develop novel compounds that are effective in the treatment of inflammatory disorders and that can be easily and safely manufactured.

SUMMARY OF THE INVENTION

Accordingly, the present invention is to provide a compound having superior effects on inhibition of proteinase 3 and neutrophil elastase and on treatment of inflammation disorders.

Initially, the present invention provides an oxime-based compound having the following formula (I) or a pharmaceutically acceptable salt thereof:

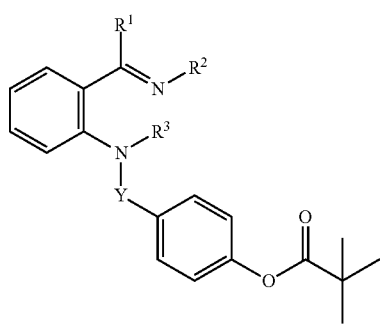

wherein:

Y is a carbonyl group or a sulfonyl group;

$R^1$ is selected from the group consisting of H, OH, a $C_1$-$C_4$ alkyl group, and a $C_1$-$C_4$ alkoxyl group;

$R^2$ is selected from the group consisting of OH, a methoxy group, —$OR^4OH$, and —is $OR^4NH_2$, $R^4$ being a $C_1$-$C_3$ alkyl group; and $R^3$ is H or a pivaloyloxybenzenesulfonyl group.

Secondly, the present invention also provides a method for preparing the oxime-based compound of formula (I), including reacting a compound of formula (A) with a compound of formula (B) and a compound of $R_2NH_2$,

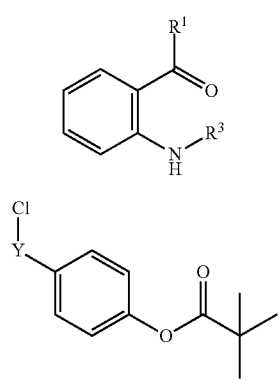

wherein $R^1$ and $R^3$ in formula (A), Y in formula (B), and $R^2$ in the compound of $R_2NH_2$ have the same definitions as $R^1$, $R^3$, Y, and $R^2$ in formula (I).

Thirdly, this invention provides a pharmaceutical composition having inhibitory activity on neutrophil elastase, including the oxime-based compound of formula (I) or the pharmaceutically acceptable salt thereof.

Fourthly, this invention provides a pharmaceutical composition having inhibitory activity on proteinase 3, including the oxime-based compound of formula (I) or the pharmaceutically acceptable salt thereof.

Fifthly, the present invention provides a pharmaceutical composition for treatment of inflammatory disorders, including the oxime-based compound of formula (I) or the pharmaceutically acceptable salt thereof.

Sixthly, this invention provides a method to inhibit neutrophil elastase activity through administering the oxime-based compound of formula (I) or the pharmaceutically acceptable salt thereof.

Seventhly, this invention provides a method to inhibit protease 3 activity through administering the oxime-based compound of formula (I) or the pharmaceutically acceptable salt thereof.

Eighthly, the present invention provides a method to treat an inflammatory disorder through administering the oxime-based compound of formula (I) or the pharmaceutically acceptable salt thereof.

BRIEF DESCRIPTION OF THE DRAWINGS

Other features and advantages of the present invention will be clarified not only via following detailed description of the preferred embodiments of this invention, but also through reference to the figures (FIG. 1-3), in which.

DETAILED DESCRIPTION

Figure 1:
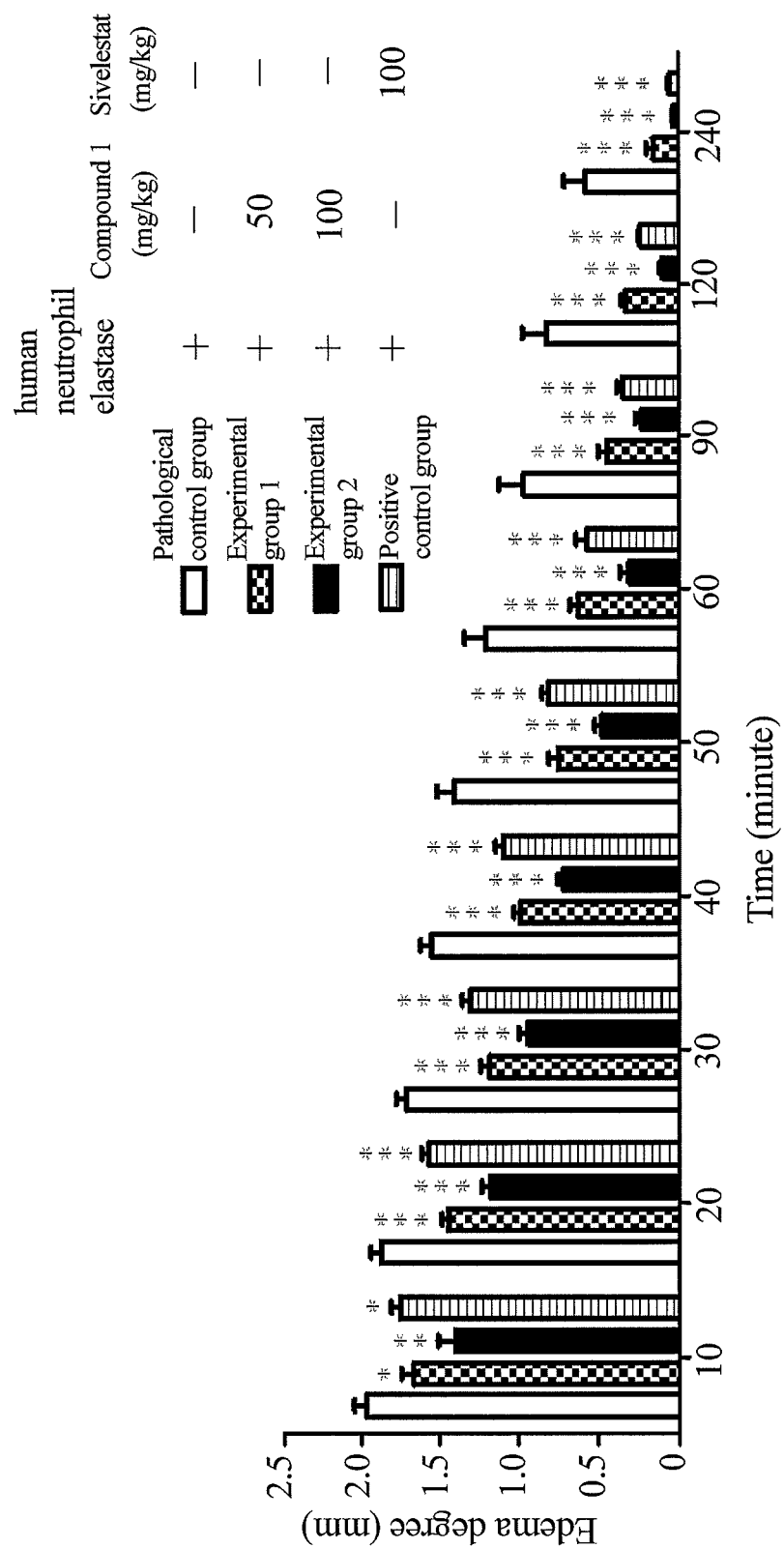
FIG. 1 shows the effect of compound (1) of an example of this invention upon the change of foot thickness of mice from each of a pathological control group (injected with human neutrophil elastase only), a positive control group (injected with human neutrophil elastase and Sivelestat) and experimental groups 1 and 2 (injected with human neutrophil elastase and compound (1)), measured using a vernier caliper at $10^{th}$, $20^{th}$, $30^{th}$, $40^{th}$, $50^{th}$, $60^{th}$, $90^{th}$, $120^{th}$ and $240^{th}$ minute after injection of human neutrophil elastase; the change of foot thickness was determined as the difference in foot thickness before and after injection of human neutrophil elastase; "*" is indicative of $p<0.05$ when compared to the pathological control group; "" is indicative of $p<0.01$ when compared to the pathological control group; and "*" is indicative of $p<0.001$ when compared to the pathological control group.

An oxime-based compound of the present invention has the following formula (I):

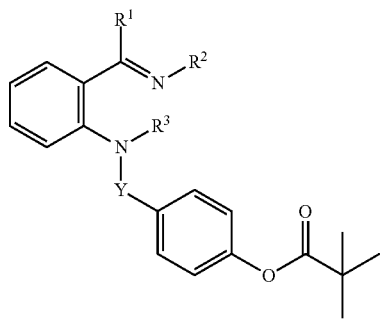

wherein:

Y is a carbonyl group or a sulfonyl group;

$R^1$ is selected from the group consisting of H, OH, a $C_1$-$C_4$ alky group, and a $C_1$-$C_4$ alkoxyl group;

$R^2$ is selected from the group consisting of OH, a methoxyl group, —$OR^4OH$, and —$OR^4NH2$, $R^4$ being a $C_1$-$C_3$ alkyl group; and $R^3$ is H or a pivaloyloxybenzenesulfonyl group.

The term "alkyl group" referred to herein is a saturated monovalent hydrocarbon group having straight chain or branched chain moieties. Thus, the term "$C_1$-$C_4$ alkyl group" referred to herein is a straight or branched saturated monovalent hydrocarbon group having 1 to 4 carbon atoms, and the term "$C_1$-$C_3$ alkyl group" referred to herein is a straight or branched saturated monovalent hydrocarbon group having 1 to 3 carbon atoms. Examples of the $C_1$-$C_4$ alkyl group include, but are not limited to, methyl, ethyl, n-propyl, iso-propyl, n-butyl, iso-butyl, sec-butyl, tert-butyl, and branched chain isomers thereof. Examples of the $C_1$-$C_3$ alkyl group include, but are not limited to, methyl, ethyl, propyl, and isopropyl.

The term "$C_1$-$C_4$ alkoxyl group" referred to herein is a group with chemical formula —OR', in which R' is a $C_1$-$C_4$ alkyl group as defined above. Examples of the $C_1$-$C_4$ alkoxy group include, but are not limited to, methoxyl, ethoxyl, n-propoxyl, iso-propoxyl, n-butoxyl, iso-butoxyl, sec-butoxyl, and tert-butoxyl.

Preferably, Y is a sulfonyl group.

Preferably, $R^1$ is H or a $C_1$-$C_4$ alkyl group.

In examples of this invention, $R^1$ is H, methyl, ethyl, or n-propyl.

Preferably, $R^2$ is OH, a methoxyl group, or —$OR^4OH$.

In examples of this invention, $R^2$ is OH, a methoxyl group, or —$OC_3H_6OH$.

The oxime-based compound of this invention is preferably selected from:

(E)-4-(N-(2-(1-(hydroxyimino)ethyl)phenyl)sulfamoyl)phenyl pivalate, (E)-4-(N-(2-(1-(hydroxyimino)propyl)phenyl)sulfamoyl)phenyl pivalate, (E)-4-(N-(2-(1-(hydroxyimino)butyl)phenyl)sulfamoyl)phenyl pivalate, (E)-4-(N-(2-((hydroxyimino)methyl)phenyl)sulfamoyl)phenyl pivalate, (E)-4-(N-(2-(1-(methoxyimino)ethyl)phenyl)sulfamoyl)phenyl pivalate, (Z)-4-(N-(2-(1-(methoxyimino)ethyl)phenyl)sulfamoyl) phenyl pivalate, and (E)-4-(N-(2-(1-(3-hydroxypropoxyimino)ethyl)phenyl)sulfamoyl)phenyl pivalate.

The oxime-based compound of the present invention can exist in free form, or where appropriate, as a pharmaceutically acceptable salt, solvate, hydrate, or stereoisomers thereof.

The pharmaceutically acceptable salt of the oxime-based compound may be, but is not limited to, a salt with an inorganic acid, such as HCl, HBr, $H_2SO_4$, and $H_3PO_4$, a salt with an organic acid, such as acetate, maleate, tartrate, and methanesulfonate, or a salt with an amino acid, such as arginine, aspartic acid, and glutamic acid.

A method for preparing the oxime-based compound of formula (I) includes:

reacting a compound of formula (A) with a compound of formula (B) and a compound of $R_2NH_2$,

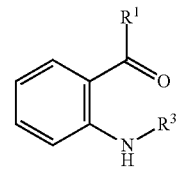

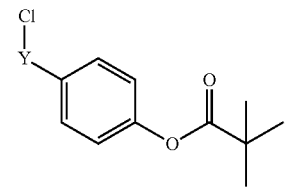

wherein $R^1$ and $R^3$ in formula (A), Y in formula (B), and $R^2$ in the compound of $R_2NH_2$ have the same definitions as $R^1$, $R^3$, Y, and $R^2$ in formula (I).

Preferably, the method is conducted by:

(a) reacting the compound of formula (A) with the compound of formula (B) so as to obtain a compound of formula (II);

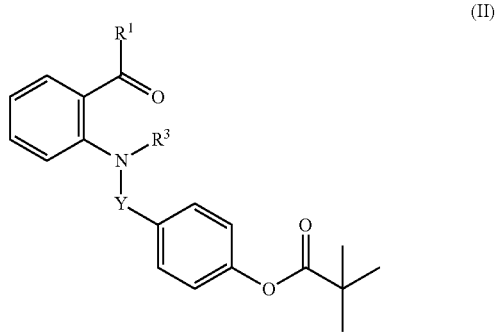

in which $R^1$ and $R^3$ in formula (II) have the same definitions as $R^1$ and $R^3$ in formula (I); and (b) reacting the compound of formula (II) with the compound of $R_2NH_2$ so as to obtain the compound of formula (I).

Preferably, the method is conducted by:

(a) reacting the compound of formula (A) with the compound of R$_2$NH$_2$ so as to form a compound of formula (III)

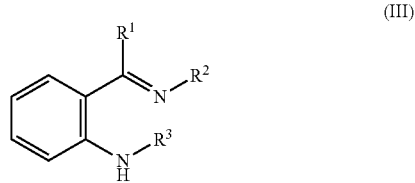

(III)

is in which R$^1$, R$^2$, and R$^3$ in formula (III) have the same definitions as R$^1$, R$^2$, and R$^3$ in formula (I); and (b) reacting the compound of formula (III) with the compound of formula (B) so as to obtain the compound of formula (I).

The oxime-based compound of formula (I) has been proven to be able to inhibit release of human neutrophil elastase and to exhibit inhibitory activity on human neutrophil elastase and protease-3 in vitro. Moreover, the oxime-based compound of formula (I) could effectively treat lipopolysaccharide (LPS)-induced acute lung injury and foot edema induced by human neutrophil elastase in vivo. The oxime-based compound of formula (I) is thus predicted to be able to treat an inflammatory disorder.

Therefore, this invention provides a pharmaceutical composition having inhibitory activity on neutrophil elastase, including the oxime-based compound of formula (I) or the pharmaceutically acceptable salt thereof. This invention also provides a pharmaceutical composition having inhibitory activity on proteinase 3, including the oxime-based compound of formula (I) or the pharmaceutically acceptable salt thereof. This invention further provides a pharmaceutical composition for treatment of an inflammatory disorder, including the oxime-based compound of formula (I) or the pharmaceutically acceptable salt thereof.

As used herein, the terms "treat," "treatment," and "treating," refer to preventing, reducing, alleviating, ameliorating, relieving, or controlling at least one of clinical signs of a disease or a disorder, or lowering, stopping, and reversing severity or progression of a condition or a symptom.

The inflammatory disorder of this invention, includes, but is not limited to, lung injury, chronic obstructive pulmonary disease, acute respiratory distress syndrome, emphysema, cystic fibrosis, focal cerebral ischemic, ischemic-reperfusion injury, glomerulonephritis, rheumatoid arthritis, bullous pemphigoid, sepsis, and Wegener's granulomatosis. (B. Korkmaz et al. (2008), *Biochimie*, 90:227-242; A. S. Cowburn et al, (2008), *Chest*, 134:606-612; Y. Nakano et al. (2009), *Journal of Surgical Research*, 155:311-317; M. Hayakawa et al. (2010), *Shock*, 33:14-18; K. J. Kwon et al. (2013), *Neurosci. Lett.*, 548:67-72; B. Korkmaz et al. (2013), *Semin. Immunopathol.*, 35:411-421; B. Korkmaz et al. (2013), *Int. Immunopharmacol.*, doi: 10.1016/j.intimp.2013.07.003). Preferably, the inflammatory disorder is lung injury, more preferably, acute lung injury.

The pharmaceutical composition of this invention may be parenterally, orally, or topically administrable and can be formulated into a dosage form, such as injection (e.g., sterile aqueous solutions, dispersions, etc.), sterile powders, tablets, troches, pills, capsules, external preparation, etc.

The pharmaceutical composition of this invention may be administered by a parenteral route, such as intraperitoneal, subcutaneous, intramuscular, or intravenous injection. In this embodiment, the pharmaceutical composition of this invention is administrated by intraperitoneal rejection.

The pharmaceutical composition of this invention further includes a pharmaceutically acceptable carrier. The pharmaceutically acceptable carrier includes at least one of the following agents: a solvent, a buffer, an emulsifier, a suspending agent, a decomposer, a disintegrating agent, a dispersing agent, a binding agent, an excipient, a stabilizing agent, a chelating agent, a diluent, a gelling agent, a preservative, a wetting agent, a lubricant, an absorption delaying agent, a liposome, etc. Examples of the pharmaceutically acceptable carrier include, but are not limited to, water, normal saline, phosphate buffered saline (PBS), a sugar-containing solution, and an aqueous solution containing alcohol.

This invention provides a method to inhibit neutrophil elastase activity or protease 3 activity in a subject, including administering the oxime-based compound of formula (I) or the pharmaceutically acceptable salt thereof to the subject. This invention also provides a method to treat an inflammatory disorder in a subject, including applying the oxime-based compound of formula (I) or the pharmaceutically acceptable salt thereof to the subject.

EXAMPLES

Preparation Examples

General Method

1. Silica gel column chromatography was conducted using a silica gel 60 (sieve mesh 230-400, available from Silicycle).

2. $^1$H-NMR and $^{13}$C-NMR were obtained using Brucker AVANCe-400 MHz FT-NMR, a nuclear magnetic resonance spectrometer. CDCl$_3$ with 7.265 ppm of δ and CDCl$_3$ with 77.0 ppm of δ were used as internal standards to determine chemical shift. Coupling constant is referred to as J, and the unit is Hz.

3. Electrospray ionization mass spectra (ESI-MS) and high-resolution electrospray ionization mass spectra (HRESI-MS) were obtained using TSQ Quantum Triple Quadrupole mass spectrometer and Orbitrap mass spectrometer respectively, both available from Thermo Finnigan LLC.

4. Preparation of oxime-based compounds of formula (I)

Compounds of formula (I) can be manufactured using one of the following Schemes 1 to 3.

In Scheme 1,2-aminobenzaldehyde or 2-aminophenyl ketone (Compound (a1)) is reacted with p-pivaloyloxybenzenesulfonyl chloride to obtain 4-(N-(2-acylphenyl)sulfamoyl) phenyl pivalate (Compound (a2)). Compound (a2) is then reacted with hydroxylamine hydrochloride to obtain the compound of formula (I). The following Compounds (1), (2), (3), and (4) in Preparation Examples 1 to 4 were prepared using Scheme 1.

Scheme 1

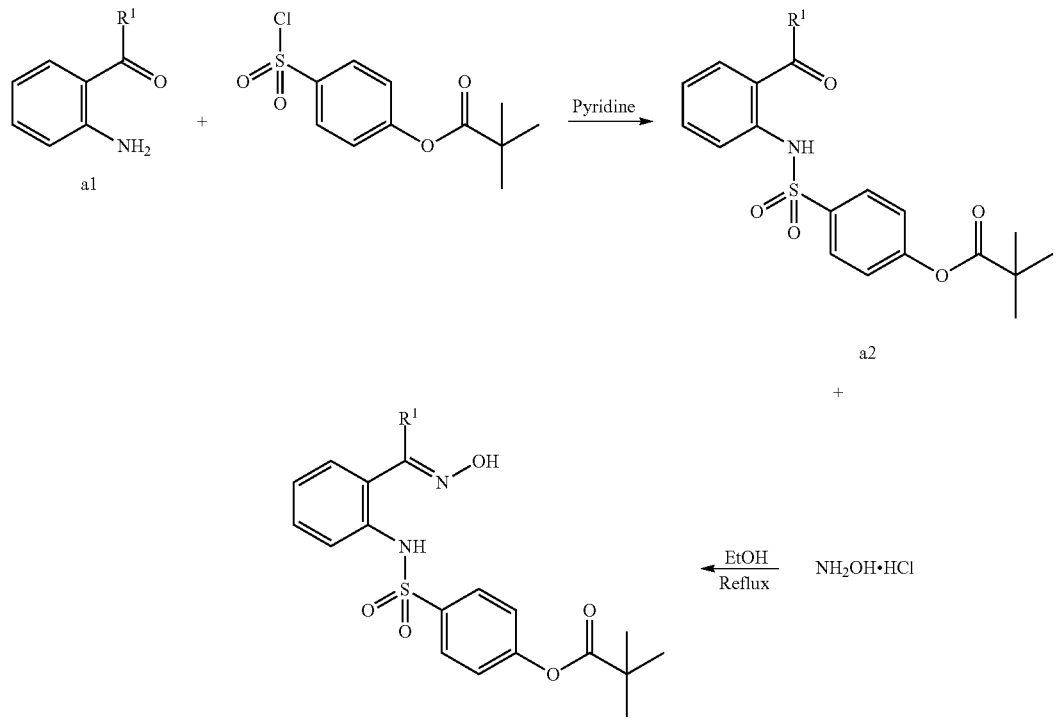

1 R¹ = CH₃
2 R¹ = CH₂CH₃
3 R¹ = CH₂CH₂CH₃
4 R¹ = H

In Scheme 2, Compound (α1) is reacted with methoxylamine hydrochloride to obtain 1-(2-aminophenyl)ethanone O-methyl oxime (Compound (a3)). Compound (a3) is then reacted with p-pivaloyloxybenzenesulfonyl chloride to obtain the oxime-based compound of formula (I). The following Compounds (5) and (6), which are geometrical isomers, in Preparation Examples 5 were prepared using Scheme 2.

Scheme 2

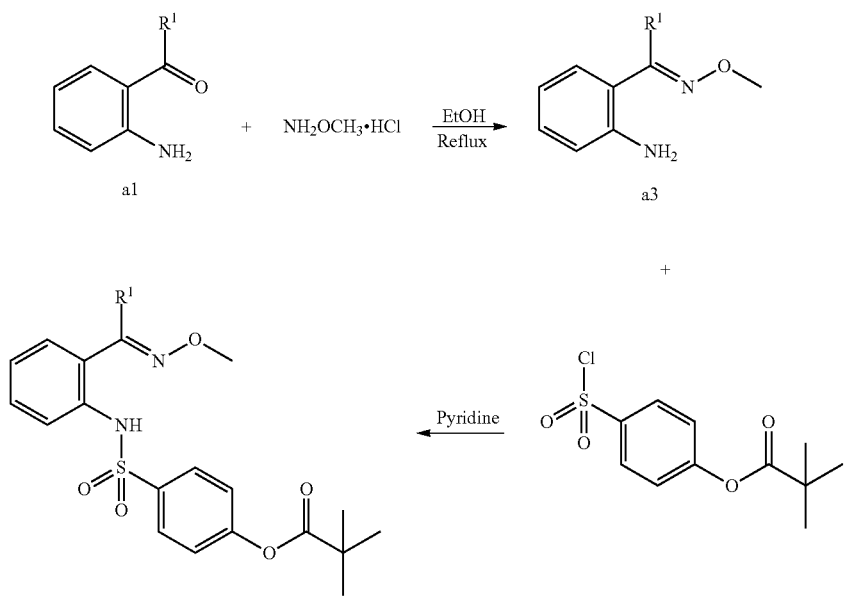

5 R¹ = CH₃
6 R¹ = CH₃

In Scheme 3, Compound (α1) is reacted with hydroxylamine hydrochloride to obtain (E)-1-(2-aminophenyl)ethanone oxime (Compound (a4)). Compound (a4) is reacted with 3-chloropropan-1-ol to obtain (E)-1-(2-aminophenyl)ethanone O-3-hydroxypropyl oxime (Compound (a5)). Compound (a5) is then reacted with p-pivaloyloxybenzenesulfonyl chloride to obtain the compound of formula (I). The following Compound (7) in Preparation Examples 6 was prepared using Scheme 3.

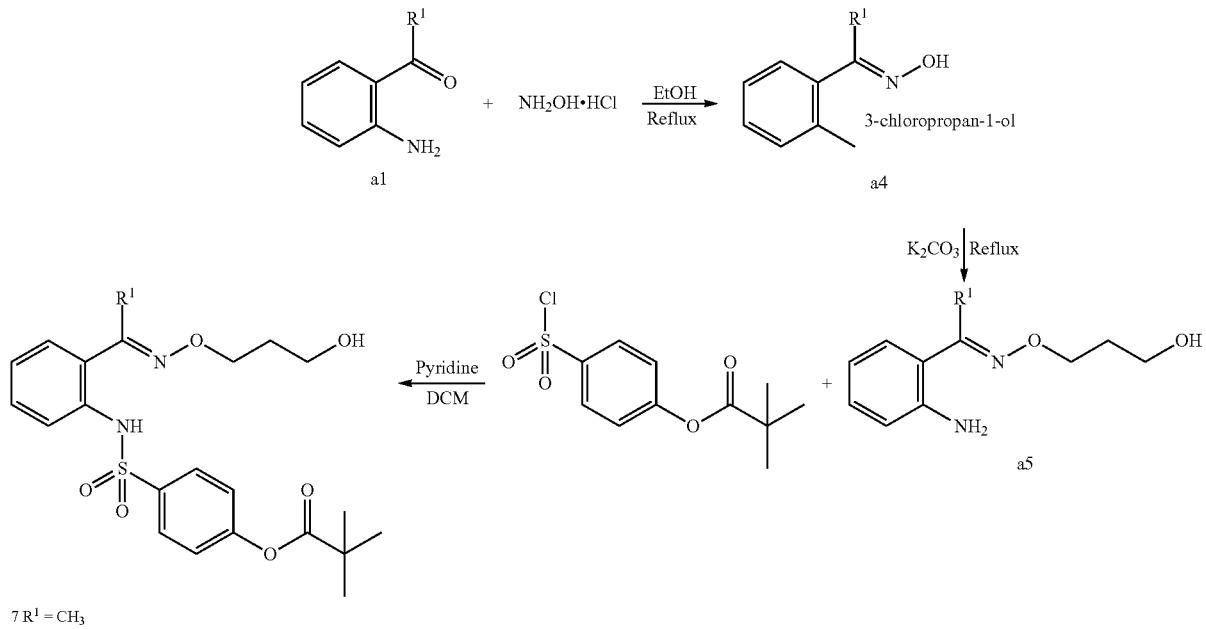

It should be noted that Compounds (1), (2), (3), and (4) can be prepared through Scheme 2, in which hydroxylamine hydrochloride is used instead of methoxylamine hydrochloride. That is, Compound (α1) is first reacted with hydroxylamine hydrochloride, followed by reacting with p-pivaloyloxybenzenesulfonyl chloride. Compound (7) also can be prepared through Scheme 2, in which O-3-hydroxypropylhydroxyamine hydrochloride is used instead of methoxylamine hydrochloride.

Preparation Example 1

Preparation of Compound (1) ((E)-4-(N-(2-(1(hydroxyimino)ethyl)phenyl)sulfamoyl)phenyl pivalate) Having the Following Formula

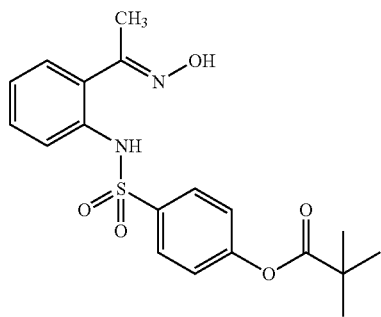

(1)

A. Preparation of 4-(N-(2-acetylphenyl)sulfamoyl)phenyl pivalate

2-Aminoacetophenone (1 mmol) and p-pivaloyloxybenzenesulfonyl chloride (1.5 equivalent weights) were added into pyridine (5 mL) to obtain a mixture, followed by subjecting to reaction at room temperature for 4 hours and then removing pyridine under vacuum to obtain a reaction product. The reaction product was purified using a silica gel column (n-hexane/acetone=4:1), thereby obtaining 4-(N-(2-acetylphenyl)sulfamoyl)phenyl pivalate (331 mg, yield 89%).

B. Preparation of Compound (1)

4-(N-(2-acetylphenyl)sulfamoyl)phenyl pivalate (0.2 mmol) and hydroxylamine hydrochloride (1.5 equivalent weights) were added into ethanol (5 mL) to obtain a mixture, followed by heating the mixture under reflux for 14 hours and then removing ethanol by vacuum concentration to obtain a reaction product. The reaction product was purified using a silica gel column (n-hexane/acetone=4:1), thereby obtaining Compound (1) as a white powder (105 mg, yield 27%).

Structure Identification $^1$H NMR (400 MHz, CDCl$_3$) δ: 10.86 (1H, s, NH), 8.51 (1H, s, OH), 7.73 (2H, d, J=8.8 Hz), 7.65 (1H, dd, J=1.2, 8.0 Hz), 7.33 (1H, dd, J=1.2, 8.0 Hz), 7.28 (1H, td, J=1.2, 8.0 Hz), 7.11 (1H, td, J=1.2, 8.0 Hz), 7.09 (2H, d, J=8.8 Hz), 2.05 (3H, s, CH$_3$), 1.33 (9H, s, (CH$_3$)$_3$); $^{13}$C-NMR (CDCl$_3$, 100 MHz) δ: 176.9 (s, —OCO—), 157.3 (s, C=N), 154.9 (s, C-4'), 136.5 (s, C-1'), 135.7 (s, C-2), 130.0 (d, C-4), 129.2 (d, C-2', 6'), 129.0 (d, C-6), 125.9 (s, C-1), 125.1 (d, C-5), 122.9 (d, C-3), 122.5 (d, C-3', 5'), 39.6 (s, C(CH$_3$)$_3$), 27.4 (q, (CH$_3$)$_3$), 12.8 (q, CH$_3$); ESI-MS: m/z 390.9 ([M+H]$^+$); HRESI-MS: m/z 391.1322 ([M+H]$^+$) (calcd. for C$_{19}$H$_{23}$O$_5$N$_2$S, 391.1330).

Preparation Example 2

Preparation of Compound (2) ((E)-4-(N-(2-(1-(hydroxyimino)propyl)phenyl)sulfamoyl)phenyl pivalate) Having the Following Formula

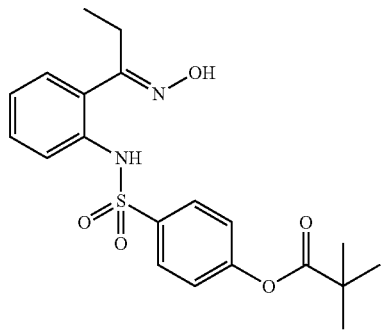

(2)

A. Preparation of 1-(2-aminophenyl)propan-1-one

2-Aminobenzonitrile (1 mmol) was disposed in anhydrous tetrahydrofuran (5 ml) is followed by adding ethylmagnesium bromide (10 equivalent weights) at 0° C. under nitrogen gas atmosphere and reacting for 4 hours to obtain a reaction product. The pH of the reaction product was adjusted to be in the range of 3 to 4 using 1N HCl, followed by partitioning using ethyl acetate and saturated $NaHCO_3$ for three times. The ethyl acetate layer was collected and purified using a silica gel column (n-hexane/acetone=4:1), thereby obtaining [1-(2-aminophenyl)propan-1-one] (83.5 mg, yield 56%).

B. Preparation of 4-(N-(2-propionylphenyl)sulfamoyl)phenyl pivalate

The procedure for preparing 4-(N-(2-propionylphenyl)sulfamoyl)phenyl pivalate is similar to procedure A in Preparation Example 1. The difference resides in that the 1-(2-aminophenyl)propan-1-one (0.5 mmol) was used to replace 2-aminoacetophenone (1 mmol). 4-(N-(2-propionylphenyl)sulfamoyl)phenyl pivalate was purified using a silica gel column (n-hexane/acetone=4:1) (263 mg, yield 68%).

C. Preparation of Compound (2)

The procedure for preparing Compound (2) is similar to procedure B in Preparation Example 1. The difference resides in that 4-(N-(2-propionylphenyl)sulfamoyl)phenyl pivalate (0.5 mmol) was used to replace 4-(N-(2-acetylphenyl)sulfamoyl)phenyl pivalate] (0.2 mmol). A silica gel column (n-hexane/acetone=4:1) was used to afford compound (2) of a white powder (153 mg, yield 37.8%).

Structure Identification $^1$H NMR (400 MHz, $CDCl_3$) δ: 11.04 (1H, s, NH), 8.40 (1H, s, OH), 7.76 (2H, d, J=8.8 Hz), 7.67 (1H, dd, J=1.2, 8.0 Hz), 7.37 (1H, dd, J=1.2, 8.0 Hz), 7.27 (1H, td, J=1.2, 8.0 Hz), 7.10 (1H, td, J=1.2, 8.0 Hz), 7.09 (2H, d, J=8.8 Hz), 2.64 (2H, q, J=7.6 Hz, CH2), 1.32 (9H, s, $(CH_3)_3$), 0.99 (3H, t, J=7.6 Hz, $CH_3$); $^{13}$C-NMR ($CDCl_3$, 100 MHz) δ: 176.4 (s, —OCO—), 161.8 (s, C=N), 154.4 (s, C-4'), 136.3 (s, C-1'), 135.9 (s, C-2), 129.6 (d, C-4), 128.8 (d, C-2', 6'), 128.3 (d, C-6), 124.4 (s, C-1), 123.6 (d, C-5), 122.0 (d, C-3, 3', 5'), 39.2 (s, C $(CH_3)_3$), 27.0 (q, $(CH_3)_3$), 19.5 (t, $CH_2CH_3$), 10.8 (q, $CH_2CH_3$); ESI-MS: m/z 405.2 ([M+H]$^+$), 427.2 ([M+Na]$^+$), 830.8 ([M+M+Na]$^+$); HRESI-MS: m/z 405.1500 ([M+H]$^+$) (calcd. for $C_{20}H_{25}O_5N_2S$, 405.1500).

Preparation Example 3

Preparation of Compound (3) ((E)-4-(N-(2-(1-(hydroxyimino)butyl)phenyl)sulfamoyl)phenyl pivalate) Having the Following Formula

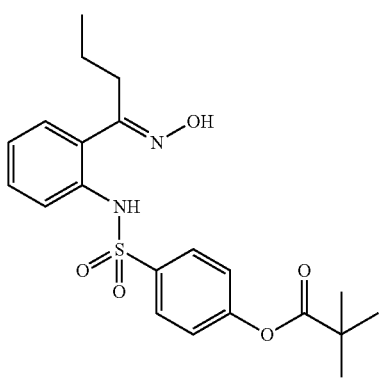

(3)

A. Preparation of 1-(2-aminophenyl)butan-1-one

The procedure for preparing 1-(2-aminophenyl)butan-1-one is similar to procedure A in Preparation Example 2. The difference resides in that propylmagnesium chloride was used to replace ethylmagnesium bromide. 1-(2-aminophenyl)butan-1-one was purified using a silica gel column (n-hexane/acetone=4:1) (91 mg, yield 56%).

B. Preparation of 4-(N-(2-butyrylphenyl)sulfamoyl)phenyl pivalate

The procedure for preparing 4-(N-(2-butyrylphenyl)sulfamoyl)phenyl pivalate is similar to procedure A in Preparation Example 1. The difference resides in that 1-(2-aminophenyl) butan-1-one (0.5 mmol) was used to replace 2-amino acetophenone (1 mmol). 4-(N-(2-butyrylphenyl)sulfamoyl) phenyl pivalate was purified using a silica gel column (n-hexane/acetone=5:1) (293 mg, yield 73%).

C. Preparation of Compound (3)

The procedure for preparing Compound (3) is similar to procedure B in Preparation Example 1. The differences reside in that 4-(N-(2-butyrylphenyl)sulfamoyl)phenyl pivalate (0.5 mmol) was used to replace 4-(N-(2-acetylphenyl)sulfamoyl) phenyl pivalate (0.2 mmol). Compound (3) was purified using a silica gel column (n-hexane/acetone=5:1), thereby obtaining Compound (3) of a white powder (292 mg, yield 70%).

Structure Identification $^1$H NMR (400 MHz, CDCl3) δ: 11.07 (1H, s, NH), 7.77 (2H, d, J=8.8 Hz), 7.68 (1H, dd, J=1.2, 8.0 Hz), 7.36 (1H, dd, J=1.2, 8.0 Hz), 7.27 (1H, td, J=1.2, 8.0 Hz), 7.10 (1H, td, J=1.2, 8.0 Hz), 7.09 (2H, d, J=8.8 Hz), 2.61 (2H, t, J=7.6 Hz, $CH_2$), 1.35 (2H, sext., J=7.6 Hz, $CH_2$), 1.32 (9H, s, $(CH_3)_3$), 0.89 (3H, t, J=7.6 Hz, $CH_3$); $^{13}$C-NMR (CDCl3, 100 MHz) δ: 176.3 (s, —OCO—), 160.8 (s, C=N), 154.4 (s, C-4'), 136.4

(s, C-1'), 136.0 (s, C-2), 129.6 (d, C-4), 128.7 (d, C-2', 6'), 128.4 (d, C-6), 124.3 (s, C-1), 123.7 (d, is C-5), 122.0 (d, C-3', 5'), 121.8 (d, C-3), 39.2 (s, C(CH$_3$)$_3$), 27.9 (t, CH$_2$CH$_2$CH$_3$), 27.0 (q, (CH$_3$)$_3$), 19.9 (t, CH$_2$CH$_2$CH$_3$), 14.2 (q, CH$_2$CH$_2$CH$_3$); ESI-MS: m/z 419.2 ([M+H]$^+$), 441.2 ([M+Na]$^+$); HRESI-MS: m/z 419.1635 ([M+H]$^+$) (calcd. for C$_{21}$H$_{27}$O$_5$N$_2$S, 419.1643).

Preparation Example 4

Preparation of Compound (4) ((E)-4-(N-(2-((hydroxyimino)methyl)phenyl)sulfamoyl)phenyl pivalate) Having the Following Formula

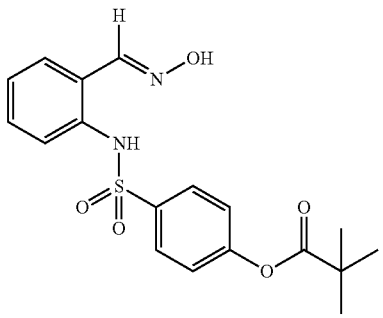

(4)

A. Preparation of 4-(N-(2-formylphenyl)sulfamoyl)phenyl pivalate

The procedure for preparing 4-(N-(2-formylphenyl)sulfamoyl)phenyl pivalate is similar to procedure A in Preparation Example 1. The difference resides in that 2-aminobenzaldehyde was used to replace 2-aminoacetophenone. 4-(N-(2-formylphenyl)sulfamoyl)phenyl pivalate was purified using a silica gel column (n-hexane/acetone=5:1) (230 mg, yield 64%).

B. Preparation of Compound (4)

The procedure for preparing Compound (4) is similar to procedure B in Preparation Example 1. The difference resides in that 4-(N-(2-formylphenyl)sulfamoyl)phenyl pivalate (0.5 mmol) was used to replace 4-(N-(2-acetylphenyl)sulfamoyl)phenyl pivalate] (0.2 mmol). Compound (4) was purified using a silica gel column (n-hexane/acetone=5:1), thereby obtaining Compound (4) of a white powder (214 mg, yield 57%).

Structure Identification $^1$H NMR (400 MHz, CDCl$_3$) δ: 10.52 (1H, s, NH), 8.05 (1H, s, H), 7.87 (2H, d, J=8.8 Hz), 7.64 (1H, br. dd, J=1.2, 8.0 Hz), 7.26 (1H, td, J=1.2, 8.0 Hz), 7.14 (2H, d, J=8.8 Hz), 7.13 (1H, dd, J=1.2, 8.0 Hz), 7.05 (1H, td, J=1.2, 8.0 Hz), 1.33 (9H, s, (CH$_3$)$_3$); $^{13}$C-NMR (CDCl$_3$, 100 MHz) δ: 176.4 (s, —OCO—), 154.6 (s, C=N), 152.1 (s, C-4'), 136.3 (s, C-1', 2), 132.1 (d, C-4), 130.5 (d, C-6), 128.9 (d, C-2', 6'), 123.7 (d, C-5), 122.2 (d, C-3', 5'), 119.5 (s, C-1), 119.1 (d, C-3), 39.2 (s, C(CH$_3$)$_3$), 27.0 (q, (CH$_3$)$_3$); ESI-MS: 399.1 ([M+Na]$^+$); HRESI-MS: m/z 399.0985 ([M+Na]$^+$) (calcd. for C$_{18}$H$_{20}$N$_2$O$_5$SNa, 399.0983).

Preparation Example 5

Preparation of Compound (5) ((E)-4-(N-(2-(1-(methoxyimino)ethyl)phenyl)sulfamoyl)phenyl pivalate) and Compound (6) ((Z)-4-(N-(2-(1-(methoxyimino)ethyl)phenyl)sulfamoyl)phenyl pivalate) Having the Following Formulas

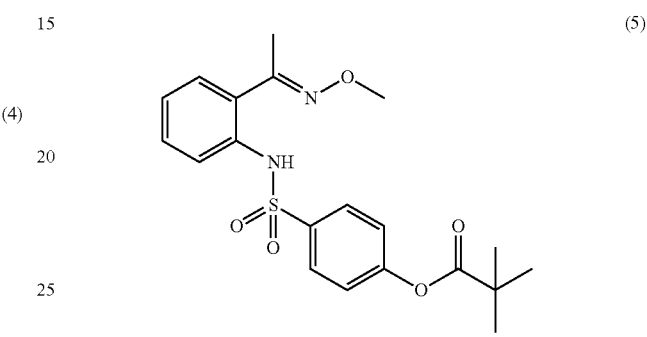

(5)

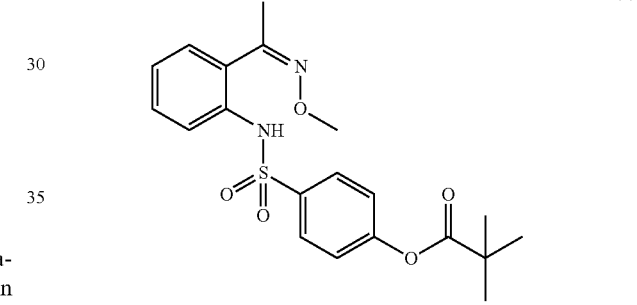

(6)

A. Preparation of 1-(2-aminophenyl)ethanone O-methyl oxime

2-Aminoacetophenone (1 mmol) was added into ethanol (10 mL), followed by adding methoxyamine hydrochloride (2.5 equivalent weights) therein to obtain a mixture. The mixture was heated under reflux for 12 hours at 80° C., followed by removal of the ethanol by vacuum concentration. The reaction product was then partitioned using water and dichloromethane (DCM) for three times. The organic layer was collected and dried with anhydrous MgSO$_4$, followed by filtration and then removal of the solvent by vacuum concentration, thereby obtaining 1-(2-aminophenyl)ethanone O-methyl oxime (154 mg, yield 94%).

B. Preparation of Compounds (5) and (6)

The procedure for preparing Compounds (5) and (6) is similar to procedure A in Preparation Example 1. The difference resides in that 1-(2-aminophenyl)ethanone O-methyl oxime (0.5 mmol) was used to replace 2-aminoacetophenone (1 mmol). Compounds (5) and (6) were purified using a silica gel column (n-hexane/acetone=4:1), thereby obtaining Compound (5) of a white powder (242 mg, yield 60%) and Compound (6) of a white powder (10 mg, yield 2.5%).

Structure Identification

Compound (5):

$^1$H NMR (400 MHz, CDCl$_3$) δ: 10.77 (1H, s, NH), 7.69 (2H, d, J=8.8 Hz), 7.65 (1H, br. dd, J=1.2, 8.4 Hz), 7.30 (1H, br, td, J=1.2, 8.4 Hz), 7.27 (1H, d, J=8.4 Hz), 7.11 (1H, td, J=1.2, 8.4 Hz), 7.08 (2H, d, J=8.8 Hz), 4.06 (3H, s, OCH$_3$), 2.02 (3H, s, CH$_3$), 1.33 (9H, s, (CH$_3$)$_3$); $^{13}$C-NMR (CDCl$_3$, 100 MHz) δ: 176.2 (s, —OCO—), 156.1 (s, C=N), 154.4 (s, C-4'), 136.4 (s, C-1'), 135.4 (s, C-2), 129.7 (d, C-6), 128.7 (d, C-2', 6'), 128.5 (d, C-4), 125.0 (s, C-1), 124.5 (d, C-5), 122.3 (d, C-3', 5'), 121.9 (d, C-3), 62.6 (q, OCH$_3$), 39.2 (s, C(CH$_3$)$_3$), 27.0 (q, (CH$_3$)$_3$), 13.2 (q, CH$_3$); ESI-MS: 403.4 ([M−H]$^-$); HRESI-MS: m/z 403.1322 ([M−H]$^-$) (calcd. for C$_{20}$H$_{23}$O$_5$N$_2$S, 403.1331).

Compound (6):

$^1$H NMR (400 MHz, CDCl$_3$) δ: 7.66 (2H, d, J=8.8 Hz), 7.64 (1H, br. dd, J=1.2, 7.6 Hz), 7.40 (1H, td, J=1.2, 7.6 Hz), 7.23 (1H, td, J=1.2, 7.6 Hz), 7.10 (2H, d, J=8.8 Hz), 7.05 (1H, d, J=1.2, 7.6 Hz), 3.91 (3H, s, OCH$_3$), 1.57 (3H, s, CH$_3$), 1.36 (9H, s, (CH$_3$)$_3$); $^{13}$C-NMR (CDCl$_3$, 100 MHz) δ: 176.3 (s, —OCO—), 154.6 (s, C=N), 153.6 (s, C-4'), 136.7 (s, C-1'), 132.7 (s, C-2), 130.3 (d, C-1), 130.1 (s, C-6), 128.8 (d, C-2', 6'), 127.3 (d, C-4), 126.5 (d, C-3), 126.3 (d, C-3), 122.3 (d, C-3', 5'), 62.1 (q, OCH$_3$), 39.2 (s, C(CH$_3$)$_3$), 27.0 (q, (CH$_3$)$_3$), 21.3 (q, CH$_3$); ESI-MS: 427.1 ([M+Na]$^+$); HRESI-MS: m/z 427.1298 ([M+Na]$^+$) (calcd. for C$_{18}$H$_{20}$N$_2$O$_5$SNa, 427.1294).

Preparation Example 6

Preparation of Compound (7) ((E)-4-(N-(2-(1-(3-hydroxypropoxyimino)ethyl)phenyl)sulfamoyl)phenyl pivalate) Having the Following Formula

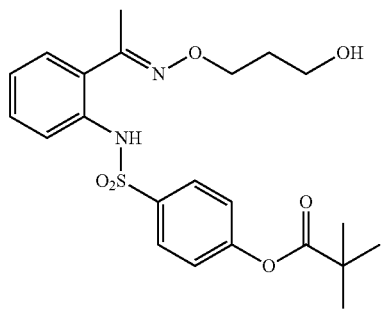

(7)

A. Preparation of (E)-1-(2-aminophenyl)ethanone oxime

2-Aminoacetophenone (1.5 mmol) and hydroxylamine hydrochloride (3.75 equivalent weights) were added into ethanol (5 mL) to obtain a mixture. The mixture was heated under reflux for 16 hours at 70° C., followed by removal of ethanol by vacuum concentration and partition using water and ethyl acetate for three times. The organic layer was collected and dried with anhydrous MgSO$_4$, followed by filtration and then removal of the solvent by vacuum concentration, thereby obtaining (E)-1-(2-aminophenyl)ethanone oxime (215 mg, yield 95%).

B. Preparation of (E)-1-(2-aminophenyl)ethanone O-3-hydroxypropyl oxime (E)-1-(2-aminophenyl)ethanone oxime (0.2 mmol) was added into anhydrous acetonitrile (MeCN) (10 mL), followed by adding K$_2$CO$_3$ (1.1 equivalent weights) and 3-chloropropan-1-ol (5 equivalent weights) therein to obtain a mixture. The mixture was heated under reflux for 36 hours and was purified using a silica gel column (n-hexane/acetone=2:1), thereby obtaining (E)-1-(2-aminophenyl)ethanone O-3-hydroxypropyl oxime (168 mg, yield 81%).

C. Preparation of Compound (7)

(E)-1-(2-aminophenyl)ethanone O-3-hydroxypropyl oxime (0.2 mmol) was added into dichloromethane (DCM) (5 mL), followed by adding pyridine (10 equivalent weights) and 4-(chlorosulfonyl)phenyl pivalate (2 equivalent weights) therein to obtain a mixture. The mixture was heated under reflux for 16 hours and was purified using a silica gel column (n-hexane/acetone=6:1), thereby obtaining Compound (7) of a white powder (43 mg, yield 49%).

Structure Identification $^1$H-NMR (CDCl$_3$, 400 MHz) δ: 10.82 (1H, s, NH), 7.71 (2H, br. dd, J=8.8 Hz, H-3', 5'), 7.63 (1H, dd, J=1.2, 8.0 Hz, H-3), 7.33 (1H, dd, J=1.2, 8.0 Hz, H-6), 7.28 (1H, td, J=1.2, 8.0 Hz, H-5), 7.09 (2H, d, J=8.8 Hz, H-2', 6'), 7.10 (1H, td, J=1.2, 8.0 Hz, H-4), 4.39 (2H, t, J=6.4 Hz, =NOCH$_2$—), 3.82 (2H, t, J=6.0 Hz, —CH$_2$OH), 3.82 (2H, t, J=6.0 Hz, —CH$_2$OH), 2.06 (2H, m, CH$_2$), 2.06 (3H, s, CH$_3$), 1.33 (9H, s, (CH$_3$)$_3$); $^{13}$C-NMR (CDCl$_3$, 100 MHz) δ: 176.3 (s, —OCO—), 156.2 (s, C=N), 154.4 (s, C-4'), 136.4 (s, C-2), 135.4 (s, C-1'), 129.7 (d, C-4), 128.6 (d, C-6), 128.6 (d, C-2', 6'), 124.8 (d, C-5), 124.4 (s, C-1), 122.0 (d, C-3', 5'), 121.7 (d, C-3), 72.1 (t, =NOCH$_2$—), 59.8 (—CH$_2$OH), 39.2 (s, C(CH$_3$)$_3$), 32.2 (t, CH$_2$), 27.0 (q, (CH$_3$)$_3$), 13.3 (q, CH$_3$); ESI-MS: 449.2 ([M+H]$^+$), 471.2 ([M+Na]$^+$); HRESI-MS: m/z 449.1761 ([M+H]$^+$) (calcd. for C$_{22}$H$_{29}$N$_2$O$_6$S, 449.1741).

Compounds (1) to (7) prepared by Preparation Examples 1 to 6 are listed in Table 1.

TABLE 1

| Comp. | IUPAC Naming | R$^1$ |
|---|---|---|
| 1 | (E)-4-(N-(2-(1-(hydroxyimino)ethyl)phenyl)sulfamoyl)phenyl pivalate | —CH$_3$ |
| 2 | (E)-4-(N-(2-(1-(hydroxyimino)propyl)phenyl)sulfamoyl)phenyl pivalate | —CH$_2$CH$_3$ |
| 3 | (E)-4-(N-(2-(1-(hydroxyimino)butyl)phenyl)sulfamoyl)phenyl pivalate | —CH$_2$CH$_2$CH$_3$ |
| 4 | (E)-4-(N-(2-((hydroxyimino)methyl)phenyl)sulfamoyl)phenyl pivalate | H |
| 5 | (E)-4-(N-(2-(1-(methoxyimino)ethyl)phenyl)sulfamoyl)phenyl pivalate] | —CH$_3$ |
| 6 | (Z)-4-(N-(2-(1-(methoxyimino)ethyl)phenyl)sulfamoyl)phenyl pivalate | —CH$_3$ |
| 7 | (E)-4-(N-(2-(1-(3-hydroxy propoxyimino)ethyl)phenyl)sulfamoyl)phenyl pivalate | —CH$_3$ |

Pharmacological Examples

The following analyses were performed in order to determine the biological activities of Compounds (1) to (7).

Experimental Materials
1. $Ca^{2+}$-free Hank's balanced salt solution:
$Ca^{2+}$-free Hank's balanced salt solution having pH 7.4 includes ingredients shown in Table 2. The ingredients were dissolved in deionized water.

TABLE 2

| Ingredient | Conc. (mg/L) |
|---|---|
| NaCl | 8000 |
| KCl | 400 |
| $KH_2PO_4$ | 60 |
| glucose | 1000 |
| $Na_2HPO_4$ | 48 |
| $MgCl_2 \cdot 6H_2O$ | 203 |

2. Hank's balanced salt solution (HBSS)
HBSS having pH 7.4 includes ingredients shown in Table 3. The ingredients were dissolved in deionized water.

TABLE 3

| Ingredient | Conc. (mg/L) |
|---|---|
| $CaCl_2 \cdot 2H_2O$ | 294 |
| NaCl | 8000 |
| KCl | 400 |
| $KH_2PO_4$ | 60 |
| glucose | 1000 |
| $Na_2HPO_4$ | 48 |
| $MgCl_2 \cdot 6H_2O$ | 203 |

3. Preparation of human neutrophil:
Healthy human volunteers (20 to 34 years old) were recruited through a certified procedure approved by Chang Gung Medical Foundation Institutional Review Board.

Blood obtained from the healthy human volunteers by venipuncture was centrifuged at 650 g for 10 minutes, and a leukocyte-rich lower layer was obtained by removing the upper layer containing platelets. 3% dextran T500 solution was well mixed with the leukocyte-rich lower layer at a volume ratio of 1:1 and was allowed to stand at room temperature. After standing for 25 minutes, the clear supernatant containing neutrophils was slowly transferred to a centrifuge tube of Ficoll-Pague™ Plus (14-1440-03, GE Healthcare, Sweden) and was subjected to density-gradient centrifugation at 400 g and 4° C. for 40 minutes. The precipitate thus obtained was treated with a hypotonic solution, i.e., 0.2% NaCl, to lyse erythrocytes, followed by removal of the lysed erythrocytes using centrifugation at 200 g and 4° C. for 8 minutes so as to obtain the neutrophils. The purified neutrophils having >98% viable cells determined using a trypan blue exclusion method was suspended in $Ca^{2+}$-free Hank's balanced salt solution (pH 7.4), thereby obtaining a neutrophil suspension having a concentration of $1 \times 10^7$ cell/ml. The neutrophil suspension was stored at 4° C. before use.

4. Experimental animals:
Male C57BL/6 mice (6 to 8 weeks of age, a body weight ranging from 20 to 25 g) were purchased from BioLasco Taiwan Co., Ltd. All mice were raised in an air-conditioned room with the following conditions: a light-dark cycle of 12 hours of illumination and 12 hours of darkness, 21-24° C., relative humidity of 40-70%, and ventilation rate at 75 to 100%. Furthermore, food and water were provided ad libitum for all of the experimental animals. All experimental procedures involving the experimental animals were approved by Laboratory Animal Center of Chang Gung University and were performed in accordance with the NIH (National Institutes of Health) Guide for the Care and Use of Laboratory Animals.

General Procedure
Statistical Analysis:
Each of the following pharmacological experiments was repeated 3 times. The experimental data are presented by "mean±standard error of the mean (SEM)." All of the data were analyzed by Student's t-test or one-way analysis of variance (one-way ANOVA), followed by turkey's test to assess the differences between groups in each pharmacological experiment. If the analytical result shows $p<0.05$, it is of statistical significance.

Pharmacological Experiment 1

Effect of Compounds (1) to (7) on Anti-Inflammation Activity

A. Effect of Compounds (1) to (7) on inhibition of elastase activity:
Each of Compounds (1) to (7) was added into 50 µL buffer A (containing 20 mM Tris-HCl (pH 7.4), 0.1% $NaN_3$ and 5 mM $CaCl_2$) to obtain compound solutions with concentrations of 0.02, 0.2, 2, or 20 µM for each of Compounds (1) to (7), followed by m adding 50 µL of the compound solutions into wells of a 96-well plate. The buffer A and Sivelestat (under the same solvent condition and concentrations as those of Compounds (1) to (7)) with the same volume were respectively used as a control group and a positive control group. Each well of the 96-well plate was further added with 25 µL of human neutrophil elastase (Enzo, 200 nM, in buffer B containing 20 mM Tris-HCl (pH 7.4) and 0.1% NaN3) and 25 µL MeO-Suc-Ala-Ala-Pro-Val-p-nitroanilide (500 µM, prepared in the buffer B), followed by reacting in an incubator (30° C.) for 30 minutes. An ELISA reader (ThermoLabsystem, USA) was used to detect the change of optical absorption at 405 nm ($OD_{405}$).

$IC_{50}$ value, indicating the concentration of the oxime-based compound that reduces 50% of absorbance at $OD_{405}$ as compared with the control group, was recorded. The results are shown in Table 4.

TABLE 4

| Compound | $IC_{50}$ (µM)[a] |
|---|---|
| 1 | 51.26 ± 7.88 |
| 2 | 679.37 ± 29.72 |
| 3 | 367.5 ± 16.69 |
| 4 | 394.44 ± 22.54 |
| 5 | 323.89 ± 38.46 |
| 6 | 367.18 ± 27.35 |
| 7 | 158.8 ± 15.50 |
| Sivelestat | 65.04 ± 4.26 |

[a]$IC_{50}$ is presented by mean ± SEM (n = 3).

It is revealed in Table 4, Compounds (1) to (7) could effectively inhibit the activity of human neutrophil elastase. Especially, Compound (1) has better inhibitory effect than Sivelestat.

B. Effect of Compounds 1 to 6 on release of human neutrophil elastase (NE):
Each of Compounds (1) to (6) was dissolved in 100% DMSO so as to obtain stock to compound solutions with concentrations of 0.01, 0.03, 0.1, 0.3, 1, 3 or 10 mM) for each of Compounds (1) to (6). 7500 of the neutrophil suspension obtained in "3. Preparation of human neutrophil" under the section of "Experimental materials" was added with 200 µM of MeO-Suc-Ala-Ala-Pro-Val-p-nitroanilide (454454, Calbiochem Limited, dissolved in 750 μl HBSS and functioned as a substrate for human neutrophils) at a is volume ratio of 1:1 (the final volume was 1.5 ml), stirred at 37° C. for 2 minutes, followed by addition with 1.5 μl of the aforesaid compound solution and reaction at 37° C. for 2 minutes. In a control group, 100% DMSO was used to substitute the compound solution. Moreover, Sivelestat (with concentrations of 0.01, 0.03, 0.1, 0.3, 1, 3 or 10 mM in DMSO) was used to substitute the compound solution as a positive control group. The reacted mixture was added with 1.5 μl of cytochalasin B (CB, 0.5 mg/ml) and was incubated for 3 minutes, followed by addition with 1.5 μl of formyl-L-methionyl-L-leucyl-L-phenylalanine (FMLP, 100 μM) and reaction for 10 minutes to activate neutrophils. Change in absorbance for the final mixture at 405 nm was measured using a spectrophotometer (U-3010, Hitachi). $IC_{50}$ value, indicating the concentration of the compound that reduces 50% of absorbance of the final mixture as compared with the control group, was recorded. The results are shown in Table 5.

TABLE 5

| Compound | $IC_{50}$ (μM)[a] |
|---|---|
| 1 | 0.03 ± 0.01 |
| 2 | 0.11 ± 0.03 |
| 3 | 0.13 ± 0.03 |
| 4 | 0.08 ± 0.02 |
| 5 | 0.17 ± 0.02 |
| 6 | 0.18 ± 0.02 |
| Sivelestat | 0.05 ± 0.001 |

[a]$IC_{50}$ is presented by mean ± SEM (n = 3).

It is found from Table 5 that Compounds (1) to (6) could effectively inhibit release of human neutrophil elastase. Especially, Compound (1) has better effect than Sivelestat.

According to the aforesaid results, since Compounds (1) to (7) could inhibit activity of human neutrophil elastase and suppress release thereof, the oxime-based compound of formula (I) is predicted to exhibit anti-inflammation activity.

Pharmacological Experiment 2

Effect of Compound (1) on Inhibition of Proteinase 3 Activity

Compound (1) was mixed with 50 μL of buffer C [containing 100 mM 4-(2-hydroxyethyl)-1-piperazineethanesulfonic acid (HEPES, pH 7.5), 500 mM NaCl, 10% DMSO and 170 mM 5,5'-dithiobis-(2-nitrobenzoic acid) (DTNB)], thereby obtaining compound solutions with concentrations of 0.02, 0.2, 2, or 20 μM). 50 μL of the compound solution was then added to each well of a 96-well plate. Sivelestat (under the same solvent condition and concentrations as those of Compound (1)) with the same volume were respectively used as a control group and a positive control. 25 μL proteinase 3 (Merck, 200 nM, prepared in buffer C) was added to each well of the 96-well plate, followed by adding 25 μL Boc-Ala-Ala-Nve-SBzl (400 μM, prepared in buffer C). The 96-well plate was disposed in an incubator at 30° C. for 180 minutes. The change in optical absorption at 405 nm ($OD_{405}$) was measured by ELISA reader.

$IC_{50}$ value, indicating the concentration of the compound that reduces 50% of absorbance of the final mixture as compared with the control group, was recorded. The results are shown in Table 6.

TABLE 6

|  | Compound 1 | Sivelestat |
|---|---|---|
| $IC_{50}$ (μM)[a] | 221.56 ± 17.31 | 338.22 ± 28.35 |

[a]$IC_{50}$ is presented by mean ± SEM (n = 3).

It is revealed From Table 6 that Compounds 1 could effectively inhibit the activity of proteinase 3, and is better in activity than Sivelestat.

According to the above results, it indicates that the oxime-based compound of formula (I) could inhibit the activities of neutrophil elastase and proteinase 3, and thus, might exhibit anti-inflammation effect and could be used to treat inflammatory disorders.

Pharmacological Experiment 3

Effect of Compounds (1) on Treatment of Foot Edema Induced by Human Neutrophil Elastase To further prove the effect of the compound (1) on treatment of inflammatory disorders, compound (1) was further subjected to an animal test. Specifically, the effect of compound (1) on treatment of foot edema of a mouse induced by human neutrophil elastase was measured.

Male C57BL/6 mice were randomly divided into four groups (n=6 for each group) including a pathological control group, a positive control group and experimental groups 1 and 2. The mice were anesthetized with pentobarbital (50 mg/kg) by intraperitoneal injection. The mice in the pathological control group and the positive control group were respectively intraperitoneally injected with 25 μL saline solution and Sivelestat (prepared in a DMSO/saline solution (v/v=7:3), 100 mg/kg dosage). The mice in experimental groups 1 and 2 were respectively and intraperitoneally injected with 25 μL of 50 mg/kg and 100 mg/kg of Compound (1) (prepared in a DMSO/saline solution (v/v=7:3)). After 60 minutes of administration, 25 μL of human neutrophil elastase (0.0075 U, 5 μg/mL, prepared in a saline solution) was injected into the rear right foot of each of the mice to induce edema in the foot.

A vernier caliper (SL-A, Insize) was used to measure the thicknesses of the rear right foot of each of the mice from each group before injection of human neutrophil elastase and at $10^{th}$, $20^{th}$, $30^{th}$, $40^{th}$, $50^{th}$, $60^{th}$, $90^{th}$, $120^{th}$ and $240^{th}$ minute after injection of human neutrophil elastase. The change in foot thickness (hereinafter referred to as edema degree) was determined by subtracting the thickness of the foot before the injection from that after the injection.

Results:

FIG. 1 shows the edema degree measured at $10^{th}$, $20^{th}$, $30^{th}$, $40^{th}$, $50^{th}$, $60^{th}$, $90^{th}$, $120^{th}$, and $240^{th}$ minute after the injection of human neutrophil elastase. As shown in FIG. 1, the mice in experimental groups 1 and 2 have relatively lower edema degree as compared to that in pathological control group. More particularly, compound (1) at 100 mg/kg exhibits superior effect in reduction of edema degree to Sivelestat. The experimental data show that compound (1) could effectively ameliorate the foot edema induced by human neutrophil elastase. Thus, the oxime-based compound of formula (I) of this invention may have in vivo anti-inflammation activity by virtue of inhibiting the activity of human neutrophil elastase, thereby achieving the treating effect on inflammatory disorders.

Pharmacological Experiment 4

Effect of Compound (1) on Treatment of Acute Lung Injury Induced by Lipopolysaccharides (LPS)

A. Induction of Acute Lung Injury

Male C57BL/6 mice were randomly divided into four groups (n=6 for each group) including a pathological control group, a positive control group, a normal control group and an experimental group. The mice were anesthetized with pentobarbital (50 mg/kg) by intraperitoneal injection. The mice from the pathological control group and the normal control group were intraperitoneally injected with 50 µL saline solution. The mice from the positive control group were intraperitoneally injected with Sivelestat [prepared in DMSO/saline solution (v/v=7:3), 100 mg/kg dosage]. The mice in the experimental group were intraperitoneally injected with compound (1) [prepared in DMSO/saline solution (v/v=7:3), 100 mg/kg dosage].

Sixty minutes after injection, each of the mice from each group was subjected to tracheostomy to form an opening in the trachea, and a PE10 catheter was inserted into the opening. Each of the mice in the normal control group was injected with 50 µL of a saline solution through the PE10 catheter. 50 µL of LPS (prepared in saline solution, 800 µL/mouse) was administered through the PE10 catheter to each of the mice in the is pathological control group, the positive control group and the experimental group, thereby causing acute lung injury.

After 6 hours of administering LPS or saline solution through the PE10 catheter, the mice were sacrificed. The chest of each of the mice was opened, and the left side of the lung was obtained by clamping the left lung hilum. 0.5 g of the retrieved left lung tissue was analyzed using the following MPO activity analysis. The rest of the left lung tissue was subjected to the following tissue pathological examination.

B. Analysis of Myeloperoxidase (MPO) Activity 0.5 g of the left lung tissue thus obtained was suspended in 2.5 mL of homogenization buffer (containing 0.5% hexadecyltrimethylammonium bromide, 0.25% protease inhibitor (P2714, Sigma) and 50 mM phosphate buffer (pH 6.0)), followed by vibrating using an ultrasonicator at 4° C. for 3 times, each time being conducted for 30 seconds, and allowing to cool on ice. The suspension was then centrifuged at 12,000 rpm and 4° C. for 10 minutes. A supernatant was collected, and the total protein concentration (mg/mL) in the supernatant was measured using a Bio-Rad assay kit.

290 µL of phosphate buffer (50 mM), 3 µL of o-dianisidine hydrochloride solution (20 g/L, as a substrate for MPO), and 3 µL of $H_2O_2$ (20 mM) was added into each well of a 96-well plate. 10 µL of the supernatant was added into each well to start reaction for 5 minutes. The reaction was stopped using 3 µL of 30% sodium azide. Absorbance ($OD_{460}$) for the reaction mixture was measured at 460 nm using an ELISA Reader. Absorbance ($OD_{460}$) was converted to MPO concentration based on a standard curve. The standard curve was obtained by plotting MPO standard solution commercially available from Sigma, St. Louis, Mo. at concentrations of 5 U/mL, 2.5 U/mL, 1.25 U/mL, 0.625 U/mL, 0.3125 U/mL, 0.15625 U/mL, and 0.078125 U/mL with the respective $OD_{460}$. The activity was determined based on the following equation:

MPO Activity (U/mg)=MPO concentration (U/ml)/ total protein concentration (mg/ml)

C. Tissue Pathological Examination

The left lung tissue of the mice from each group was rinsed with PBS and was fixed using a fixating solution (10% paraformaldehyde prepared in PBS) for 24 hours, followed by subjecting to ethanol dehydration treatment. The dehydrated tissue was then embedded in paraffin and sliced, thereby obtaining a sample with 4 to 6 µm thickness. The paraffin was then removed from the sample. The tissue was then stained with hematoxylin and eosin, was observed using an optical microscope (IX81, Olympus) at 400× magnification, and an image thereof was captured using a digital camera (DP72, Olympus).

Results:

a. Analysis of MPO Activity

Figure 2:
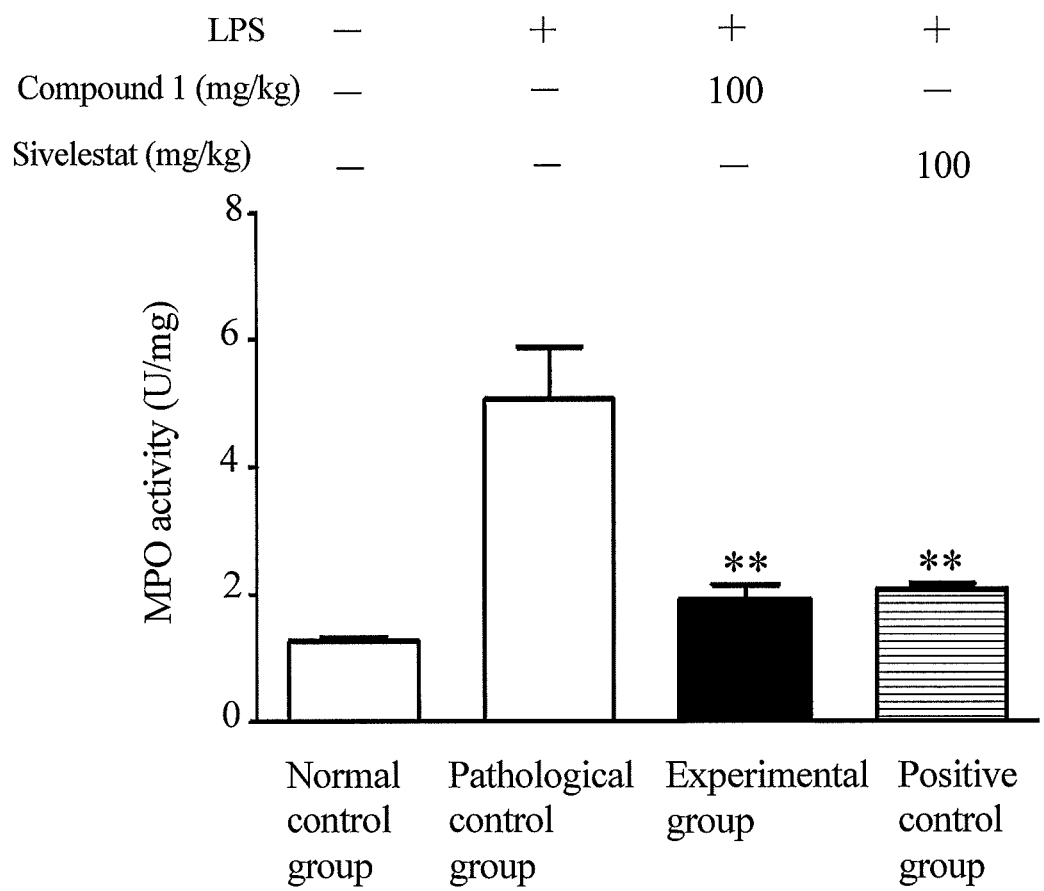
FIG. 2 shows the effect of compound (1) on myeloperoxidase (MPO) activity in lung tissues of mice from each of a normal control group (injected with a saline solution but not administered with LPS), a pathological control group (injected with a saline solution and administered with LPS), a positive control group (administered with LPS and injected with Sivelestat) and an experimental group (administered with LPS and injected with Compound (1)); "" is indicative of $p<0.01$ when compared to the pathological control group.

Referring to FIG. 2, it is revealed that, compared to the normal control group, the MPO activity in the pathological control group is increased, indicating that LPS successfully induces the acute lung injury in the mice. The data also show that, compared with the pathological control group, administration of compound (1) to the mice in the experimental group significantly reduced MPO activity, and compound (1) has an effect comparable to that of Sivelestat.

B. Tissue Pathological Examination

Figure 3:
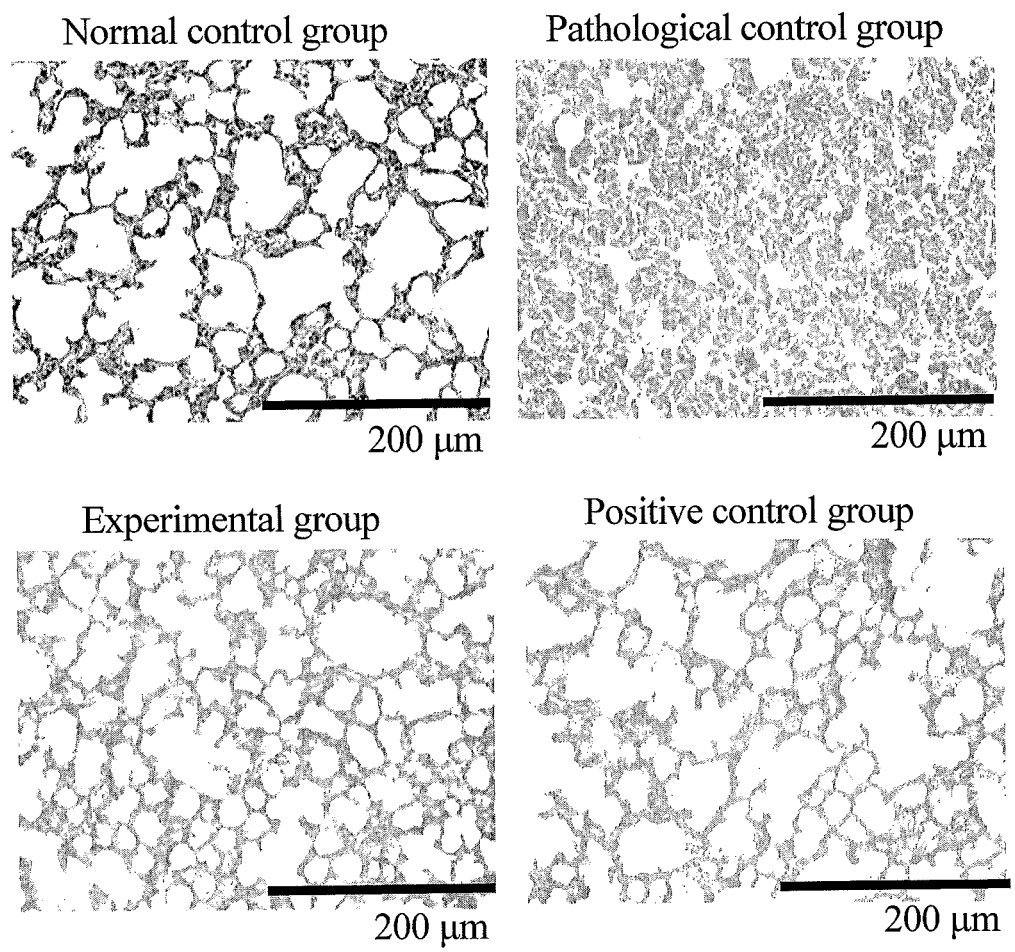
FIG. 3 shows pictures of lung tissues from the mice in the normal control group, the pathological control group, the positive control group and the experimental group of FIG. 2**, observed using an optical microscope (IX81, Olympus) at 400× magnification and captured using a digital camera (DP72, Olympus).

FIG. 3 shows pictures of the lung tissues in the pathological control group, the positive control group, the normal control group and the experimental group. It is revealed that, in the pathological control group, alveolar edema, interstitial lung edema, and leukocyte infiltration were observed, showing that LPS successfully induced acute lung injury in the mice. Compared with the pathological control group, the lung tissue of the experimental group shows minor alveolar edema, interstitial lung edema, and leukocyte infiltration.

According to the aforesaid experimental results, it is evident that compound (1) could effectively improve the LPS induced-acute lung injury.

In conclusion, the oxime-based compound of formula (I) has superior inhibitory activities on neutrophil elastase and proteinase 3, and exhibits ability to ameliorate LPS-induced actue lung injury and foot edema induced by human neutrophil elastase in vivo, indicating that the oxime-based compound of formula (I) may be a potential drug for the treatment of inflammatory disorders by regulation of the activity of neutrophil elastase and proteinase 3.

While the present invention has been described in connection with what are considered the most practical and preferred embodiments, it is understood that this invention is not limited to the disclosed embodiments but is intended to cover various arrangements included within the spirit and scope of the broadest interpretation and equivalent arrangements.

The invention claimed is:

1. An oxime-based compound having the following formula (I) or a pharmaceutically acceptable salt thereof:

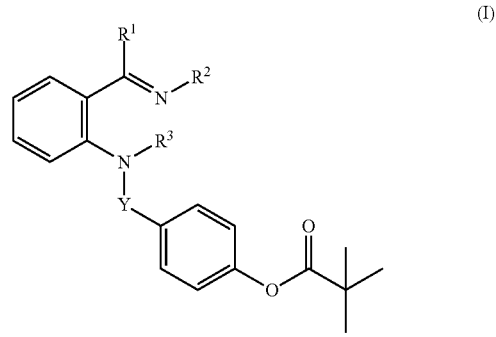

(I)

wherein:

Y is a carbonyl group or a sulfonyl group;

$R^1$ is selected from the group consisting of H, OH, a $C_1$-$C_4$ alkyl group, and a $C_1$-$C_4$ alkoxyl group;

$R^2$ is selected from the group consisting of OH, a methoxyl group, —$OR^4OH$, and —$OR^4NH2$, $R^4$ being a $C_1$-$C_3$ alkyl group; and $R^3$ is H or a pivaloyloxybenzenesulfonyl group.

2. The oxime-based compound of claim 1, wherein Y is a sulfonyl group.

3. The oxime-based compound of claim 1, wherein $R^1$ is selected from the group consisting of H and a $C_1$-$C_4$ alkyl group.

4. The oxime-based compound of claim 3, wherein $R^1$ is selected from the group consisting of H, methyl, ethyl, and n-propyl.

5. The oxime-based compound of claim 1, wherein $R^2$ is selected from the group consisting of OH, a methoxyl group, and —$OR^4OH$.

6. The oxime-based compound of claim 5, wherein —$OR^4OH$ of $R^2$ is —$OC_3H_6OH$.

7. The oxime-based compound of claim 1, selected from the group consisting of:
(E)-4-(N-(2-(1-(hydroxyimino)ethyl)phenyl)sulfamoyl) phenyl pivalate,
(E)-4-(N-(2-(1-(hydroxyimino)propyl)phenyl)sulfamoyl) phenyl pivalate,
(E)-4-(N-(2-(1-(hydroxyimino)butyl)phenyl)sulfamoyl) phenyl pivalate,
(E)-4-(N-(2-((hydroxyimino)methyl)phenyl)sulfamoyl) phenyl pivalate,
(E)-4-(N-(2-(1-(methoxyimino)ethyl)phenyl)sulfamoyl) phenyl pivalate,
(Z)-4-(N-(2-(1-(methoxyimino)ethyl)phenyl)sulfamoyl) phenyl pivalate, and
(E)-4-(N-(2-(1-(3-hydroxypropoxyimino)ethyl)phenyl) sulfamoyl)phenyl pivalate.

8. A pharmaceutical composition having inhibitory activity on neutrophil elastase, comprising the oxime-based compound of claim 1 or the pharmaceutically acceptable salt thereof.

9. A pharmaceutical composition having inhibitory activity on proteinase 3, comprising the oxime-based compound of claim 1 or the pharmaceutically acceptable salt thereof.

10. A pharmaceutical composition for treatment of an inflammatory disorder, comprising the oxime-based compound of claim 1 or the pharmaceutically acceptable salt thereof.

11. The pharmaceutical composition of claim 10, wherein the inflammatory disorder is selected from the group consisting of: lung injury, chronic obstructive pulmonary disease, acute respiratory distress syndrome, emphysema, cystic fibrosis, focal cerebral ischemic, ischemic-reperfusion injury, glomerulonephritis, rheumatoid arthritis, bullous pemphigoid, sepsis, and Wegener's granulomatosis.

12. The pharmaceutical composition of claim 11, wherein the inflammatory disorder is lung injury.

13. The pharmaceutical composition of claim 12, wherein the inflammatory disorder is acute lung injury.

14. A method for preparing the oxime-based compound of claim 1, comprising:
reacting a compound of formula (A) with a compound of formula (B) and a compound of $R_2NH_2$,

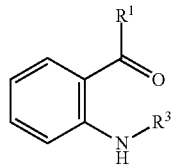

(A)

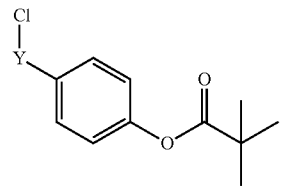

(B)

wherein $R^1$ and $R^3$ in formula (A), Y in formula (B), and $R^2$ in the compound of $R_2NH_2$ have the same definitions as $R^1$, $R^3$, Y, and $R^2$ in formula (I).

15. The method of claim 14, which is conducted by:
(a) reacting the compound of formula (A) with the compound of formula (B) so as to obtain a compound of formula (II);

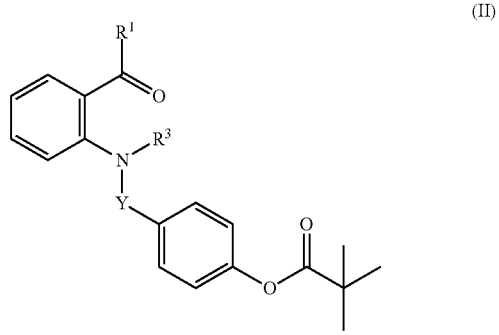

(II)

in which $R^1$ and $R^3$ in formula (II) have the same definitions as $R^1$ and $R^3$ in formula (I); and (b) reacting the compound of formula (II) with the compound of $R_2NH_2$ so as to obtain the compound of formula (I).

16. The method of claim 14, which is conducted by:
(a) reacting the compound of formula (A) with the compound of $R_2NH_2$ so as to form a compound of formula (III)

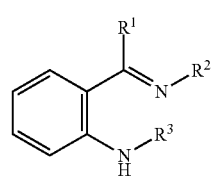

(III)

in which $R^1$, $R^2$, and $R^3$ in formula (III) have the same definitions as $R^1$, $R^2$, and $R^3$ in formula (I); and (b) reacting the compound of formula (III) with the compound of formula (B) so as to obtain the compound of formula (I).

* * * * *